United States Patent [19]

Rajasekaran

[11] Patent Number: 5,411,872
[45] Date of Patent: May 2, 1995

[54] METHOD FOR TRANSFECTED CELL SELECTION

[75] Inventor: Ayyappan K. Rajasekaran, New York, N.Y.

[73] Assignee: Cornell Research Foundation, Inc., Ithaca, N.Y.

[21] Appl. No.: 118,046

[22] Filed: Sep. 8, 1993

[51] Int. Cl.⁶ .................... C12Q 1/24; C12Q 1/04; C12N 5/00
[52] U.S. Cl. ........................ 435/30; 435/34; 435/240.241
[58] Field of Search .............. 435/30, 34, 240.241, 435/284, 292, 297–299, 803; 424/94.64

[56] References Cited

U.S. PATENT DOCUMENTS

| | | | |
|---|---|---|---|
| 4,237,223 | 12/1980 | Metz | 435/30 |
| 4,304,866 | 12/1981 | Green | 435/240 |
| 4,684,613 | 8/1987 | Barrere | 435/301 |
| 5,137,812 | 8/1992 | Matner | 435/38 |

OTHER PUBLICATIONS

Klebe R., Cultivation of Mammalian Cells in Heat-Sealable . . . Exp Cell Research '88 pp. 316–319 1990.
Costar Catalog 1992, Cambridge Mass. (800) 492–1110.

Primary Examiner—William H. Beisner
Assistant Examiner—Ralph Gitomer
Attorney, Agent, or Firm—Perman & Green

[57] ABSTRACT

A method for selecting transfected cell clones employs a transparent container that includes a lower-most surface that is covered with a transparent, thin sheet. The method includes the steps of: growing transfected cell clones on the transparent sheet within a growth medium in the transparent container; excising areas of the transparent sheet that support a transfected cell clone; and placing the excised transfected cell clone in a cell growth medium for further replication. The transparent sheet contained within the transparent container is provided with a peripheral adhesive area that enables it to remain in place when a transfected cell clone is excised.

3 Claims, 1 Drawing Sheet

METHOD FOR TRANSFECTED CELL SELECTION

This invention was made with Government support under Grant No. GM-34107-10, awarded by the National Institutes of Health. The Government has certain rights in the invention.

FIELD OF THE INVENTION

This invention relates to a method and apparatus for selecting cell colonies which have taken up a foreign DNA (transfected cell colonies) and, more particularly, to a method and apparatus for segregating such cell colonies and placing them into growth media for replication.

BACKGROUND OF THE INVENTION

Introduction of foreign genes into eukaryotic cells (transfection) is a commonly-used technique in molecular biology and cell biology laboratories. There are two different types of transfection: (1) transient transfection where introduced genes are studied for a short period of time; or (2) stable transfection where genes are introduced permanently into cell lines. The stable transfection process requires a selection of the transfected cells for further replication and studies.

The transfection process commences with an initial growth of a culture of eukaryotic cells in a liquid medium in a culture dish. A foreign DNA, with which the eukaryotic cells are to be transfected, is prepared using a calcium phosphate coprecipitation method or another equivalently effective method, to obtain a DNA precipitate. The liquid medium is removed from the culture dish and the foreign DNA precipitate is added to the eukaryotic cells. At the same time, a marker DNA precipitate is added that will enable subsequent selection of the Eukaryotic cells that uptake the DNA inclusions. In general, the marker DNA includes a gene that codes for an enzyme that will provide resistance to a drug for the cells which uptake the marker DNA (and the foreign DNA). For example, if the drug Neomycin will be used to select the transfected cells, then a Neomycin resistant gene will be used as the marker DNA during transfection.

Once the cells have had both the marker and foreign DNA precipitates added to the cell culture, the cell culture is allowed to grow for a period of time. Then, the cells are fed with a medium containing an appropriate drug. Only those cells that took up the marker DNA (and foreign DNA) are resistant to the toxic effect of the drug and grow in its presence. Non-transfected cells die. This procedure takes approximately 15-20 days. Once the non-transfected cells are dead, the growth of the transfected cells can be visualized as distinct small groups of cells (clones) in the culture dish. The clones now must be transferred to another dish for replication and further study.

The conventional method for segregation of transfected cell clones is illustrated in FIG. 1. A culture dish 10 includes a culture medium 12 in which clones 14 have been grown, after transfection. Initially, the laboratory technician views culture dish 10 from below (as indicated by arrow 16) and employing a felt marker, marks each of the clones on the bottom of culture dish 10 so as to enable identification of the clones from above. Next, culture medium 12 is removed and a cloning ring 18 (which is a glass cylinder having a silicone grease coating at least about its lower aperture) is placed over a colony and is affixed firmly to the bottom of culture dish 10. A trypsin solution is then added into the well of cloning ring 18 and causes the cells of the clone to separate from the bottom of culture dish 10. The grease coating on the bottom of cloning ring 18 prevents leakage of the trypsin solution from within the cloning ring's well. At this point, the lab technician aspirates the trypsin/clone from the well and places the aspirant into another dish containing medium, for further growth.

The above described procedure exhibits a number of disadvantages which make the process both time consuming and inefficient in the recovery of cloned cells. In order to fix cloning ring 18 to the bottom of culture dish 10, the culture medium is first removed. The cell clones, as a result, immediately start to dry. After a few cloning rings have been affixed and cells of a few clones removed, the remaining clones on the dish often have dried out and have become useless. The trypsin solution added to a cloning ring 18 may leak out if the cloning ring does not make a good seal with culture dish 10. Further, the trypsin solution is not completely effective in removing all of the cells of a clone from the bottom of culture dish 10, so there are some cloned cells that are not recoverable. Finally, cloning rings are expensive and require organic solvents for cleaning. Disposal of such solvents is a continuing problem.

Accordingly, it is an object of this invention to provide an improved method for transfected cell selection.

It is another object of this invention to provide a rapid method for transfected cell selection that eliminates a need for cloning rings.

It is yet another object of this invention to provide an apparatus for transfected cell selection that enables improvements in the recovery of stably transfected cells.

SUMMARY OF THE INVENTION

A method for selecting transfected cell colonies employs a transparent container that includes a lower-most surface that is covered with a transparent, thin sheet. The method comprises the steps of: growing transfected cell clones on the transparent sheet within a growth medium in the transparent container; excising an area of the transparent sheet that supports a clone of transfected cells; and placing the excised clone in a cell growth medium for further replication. The transparent sheet contained within the transparent container is provided with a peripheral adhesive area that adheres to the bottom of the container and enables the sheet to remain in place when a transfected cell clone is excised.

DETAILED DESCRIPTION OF THE INVENTION

Figure 1:
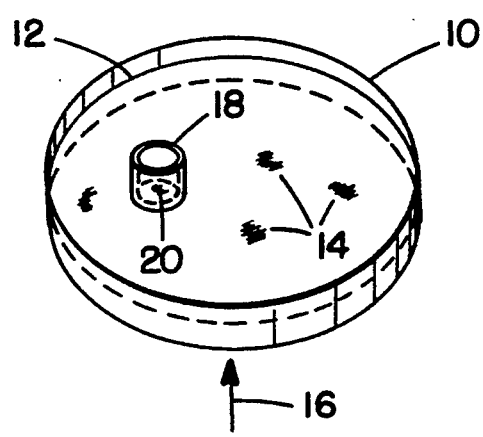
FIG. 1 is perspective view of a prior art apparatus employed to segregate transfected cell clones.
Figure 2:
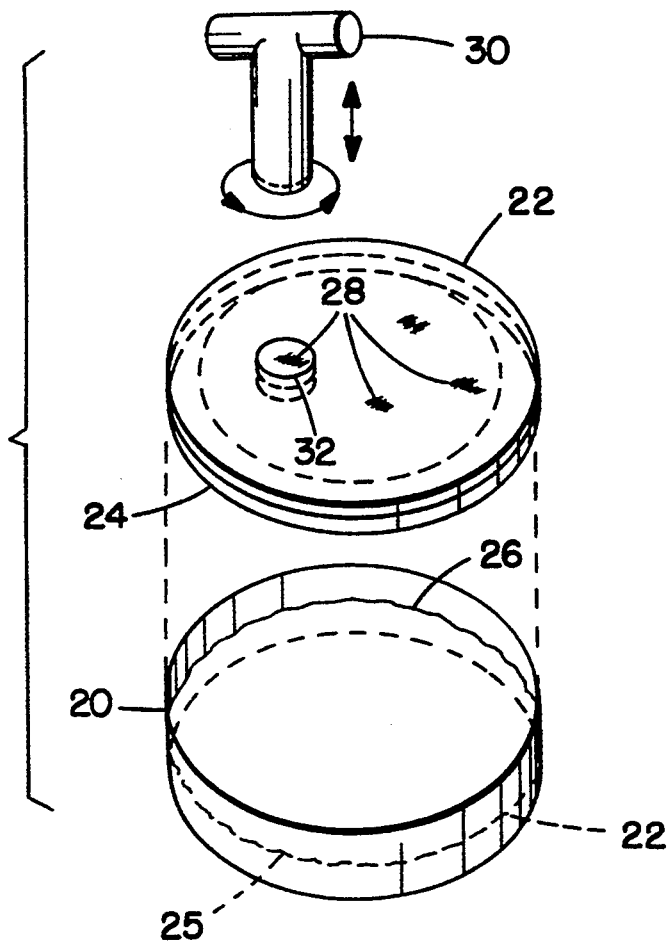
FIG. 2 is an exploded view of apparatus employing the invention and enabling transfected cell clone selection.

Referring to FIG. 2, a culture dish 20 has had placed therein, a thin transparent sheet 22. Sheet 22 is shown both removed from culture dish 20 to enable its visualization and in place in culture dish 20 (dashed). Sheet 22 is preferably transparent and includes a peripheral area of adhesive 24 positioned on its underside. When sheet 22 is placed within culture dish 20, it resides in contact with bottom surface 25 and is adherent about the periphery of bottom surface 25. A culture medium 26 is present within culture dish 20 and covers transparent sheet 22.

Sheet 22 is preferably comprised of a transparent film-forming material such as cellophane, polypropylene, polyethylene, etc. The material of which sheet 22 is comprised needs to allow visualization of cell cultures grown thereon from the underside of culture dish 20; to be receptive to cell growth on its uppermost surface and to be susceptible to excision. Sheet 22 may be exactly shaped to fit bottom surface 25 or may extend up and over the sides of culture dish 20. Sheet 22 may also be treated to enhance tissue culture growth with agents such as polysine, poly-lysine, collagen or matrigel, etc.

The procedure described in the Background of the Invention relating to the preparation of transfected cell clones is followed, using the structure shown in FIG. 2. In specific, eukaryotic cells are emplaced within culture dish 20, grown, and then are transfected with both foreign and marker DNA precipitates. After transfection, the cells are fed with a medium containing an appropriate drug that attacks cells that have not taken up the foreign and marker DNA's. Only those cells that take up the marker DNA are resistant to the toxic effect of the drug and grow in its presence to create clones of transfected cells 28 on the uppermost surface of sheet 22. When sufficient time has passed to enable growth of clones 28 (to a point where they become visible), a cylindrical hole borer 30 is employed to cut a "plug" 32 from sheet 22 while it is still immersed within culture medium 26.

Figure 3:
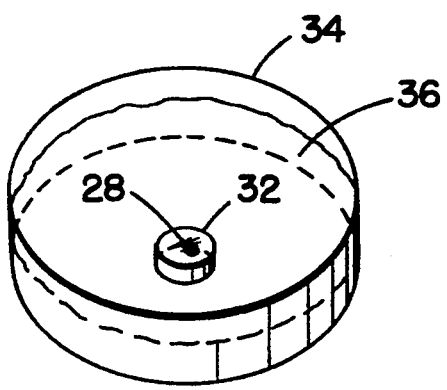
FIG. 3 is a perspective view of a dish containing a growth medium and into which an excised, transfected cell clone has been placed for further replication.

Next, plug 32 is removed (e.g. by use of a tweezers) and placed in a further cell culture dish 34 (see FIG. 3) containing trypsin which enables clone cells 28 to separate from plug 32. A cell culture medium 36 is added to culture dish 34 to enable further growth of the detached clone cells. Plug 32 is discarded.

As an alternative procedure, medium 36 may be simply a cell culture media, without trypsin, and a spatula may be employed to gently remove clone cell colony 28 from the surface of plug 32. Such removal can occur while plug 32 is immersed in cell culture 36 or in any other manner which retains the viability of clone cell colony 28.

The above procedure is repeated for each clone 28 until all have been segregated and placed into separate cell culture dishes. Those skilled in the art will realize that this procedure enables individual clones to be removed from sheet 22 while the remaining clones are still immersed in culture medium 26. Furthermore, the cloned cells that are adherent to plug 32 are not removed until after plug 32 has been removed from culture dish 20, thereby preventing cross contamination of other cloned cells. Furthermore, improved cell recovery can be achieved by a combination of both mechanical (e.g. scraping) and enzymatic (e.g. trypsinization) treatment of the removed plug. The method also easily enables removal of clones of various sizes. Further, when the size of the clone is big enough (e.g. >5 mm) the clone can be divided, with one part used for replication and the other part used for immunofluorescent analysis to check on the expression of the introduced foreign gene. Finally, the use of solvents or grease, as employed in the prior art is avoided entirely.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method for selecting transfected cell clones from a growth medium, said growth medium contained within a transparent container which includes a surface that is covered with a transparent, thin sheet which is at least partially adhered to said surface, said method comprising the steps of:
   (a) transfecting a cell population with foreign DNA;
   (b) growing said cell population transfected in step (a) on said transparent sheet within said growth medium and in said transparent container;
   (c) adding a drug to said transfected cell population to kill untransfected cells;
   (d) growing remaining transfected cell clones on said transparent sheet within a growth medium and in said transparent container;
   (e) excising an area of said transparent sheet that contains a transfected cell clone; and
   (f) placing said transfected cell clone carried by the area of the transparent sheet excised in step (e) in a cell growth medium.

2. The method as recited in claim 1, wherein step (f) comprises the substeps of:
   (f1) lacing the excised area of said transparent sheet that contains said transfected cell clone into a growth medium containing trypsin so that said transfected cell clone is in contact with said growth medium containing trypsin; and
   (f2) removing said excised area of said transparent sheet from said growth medium containing trypsin after said transfected cell clone has separated therefrom.

3. The method as recited in claim 1, wherein step (f) includes the substep of:
   (f1) scraping the transfected cell clone from the area of said transparent sheet that is excised in step (e) into said cell growth medium.

* * * * *